United States Patent [19]

Yen et al.

[11] Patent Number: 5,017,495

[45] Date of Patent: May 21, 1991

[54] **PLASMID ENCODING THE *PSEUDOMONAS MENDOCINA* TOLUENE MONOOXYGENASE GENE**

[75] Inventors: Kwang-Mu Yen, Thousand Oaks; Lawrence M. Blatt, Sherman Oaks, both of Calif.

[73] Assignee: Amgen Inc., Thousand Oaks, Calif.

[21] Appl. No.: 177,631

[22] Filed: Apr. 5, 1988

[51] Int. Cl.$^5$ .......................... C12N 1/00; C12N 9/02; C12N 1/22; C12P 21/06; C12P 21/04; C12R 1/38

[52] U.S. Cl. ................................ 435/320.1; 435/69.1; 435/11.2; 435/189; 435/252.34; 435/874; 935/16; 935/29; 935/39; 935/56; 935/61; 935/72; 935/82

[58] Field of Search .................. 435/121, 172.1, 172.3, 435/252.34, 262, 253.3, 320, 874, 877; 935/14, 29, 56, 72

[56] References Cited

PUBLICATIONS

Whited, G. M., Ph.D. Thesis, Univ. of Texas at Austin, Dissertation Abstracts International, p. 1861, vol. 47/05-B, (1986).

*Primary Examiner*—Robin L. Teskin
*Assistant Examiner*—Joan Ellis
*Attorney, Agent, or Firm*—Allegretti & Witcoff

[57] ABSTRACT

Disclosed and claimed are DNA gene segments, biologically functional plasmids and recombinant plasmids, and microorganism host cells containing such plasmids, all of which contain toluene monooxygenase genes from *Pseudomonas mendocina* KR-1 and which are useful in a method for the microbial bioconversion of selected phenyl compounds to selected phenolic compounds. In particular, the method is useful for making p-hydroxyphenylacetic acid which is a valuable chemical intermediate in the preparation of certain antibiotics and certain β-adrenergic blocking agents.

21 Claims, 3 Drawing Sheets

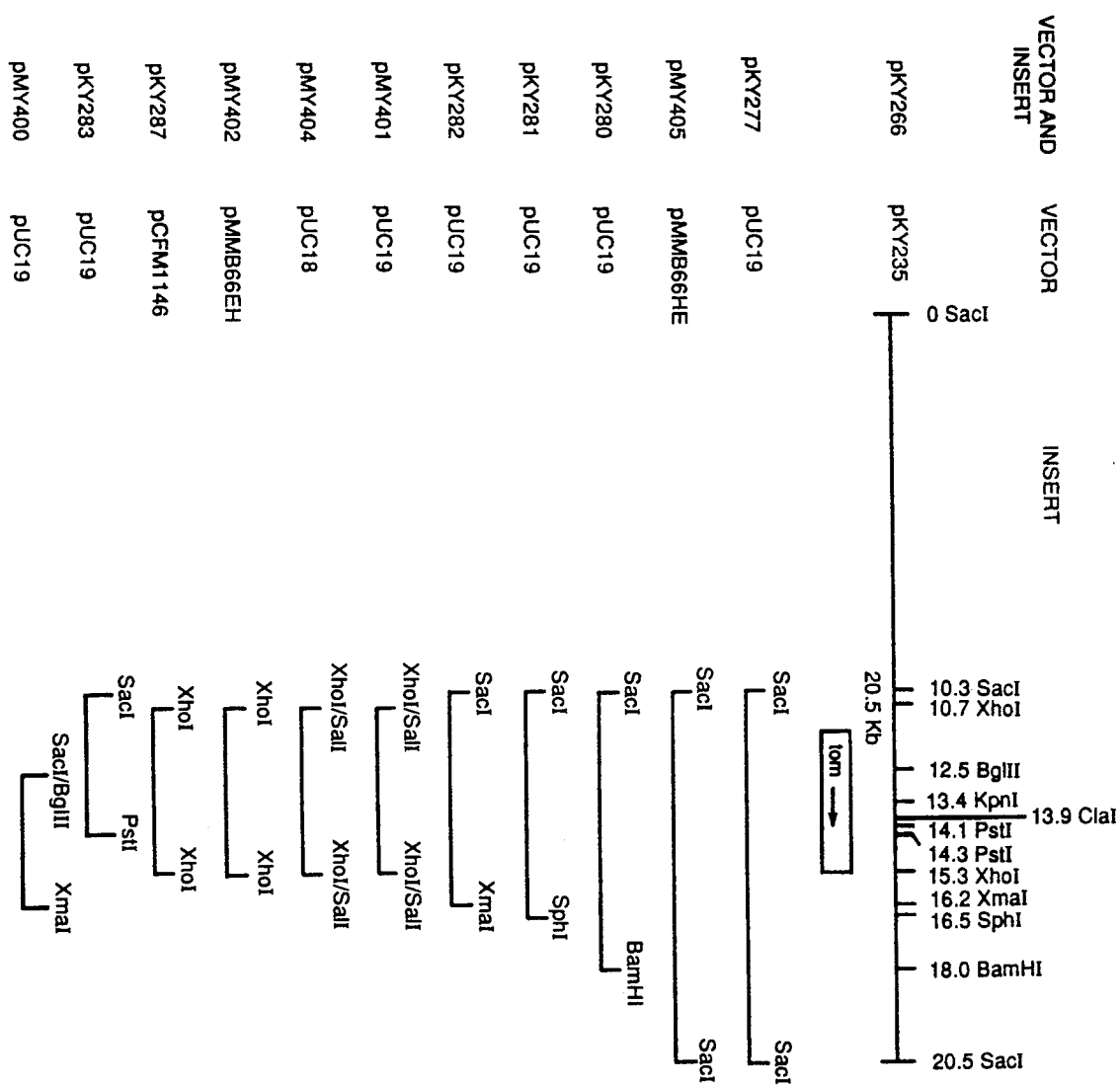

PLASMID ENCODING THE *PSEUDOMONAS MENDOCINA* TOLUENE MONOOXYGENASE GENE

BACKGROUND OF THE INVENTION

The present invention is directed to the use of recombinant DNA techniques to confer upon microorganism host cells the capacity for selected bioconversions. More specifically, the invention is directed to the cloning of toluene monooxygenase genes from a newly isolated and characterized *Pseudomonas* strain, *Pseudomonas mendocina* KR-1. The present invention thus provides genetically engineered microorganisms that over produce toluene monooxygenase enzymes and proteins, and therefore provides more efficient means of conducting bioconversions dependent on this enzyme system.

Recently, a bacterium identified as *Pseudomonas mendocina* KR-1 (PmKR1) was isolated by Richardson and Gibson from an algal-mat taken from a fresh water lake. Whited, Ph. D. Dissertation, The University of Texas at Austin, Library Reference No. W586 (1986). PmKR1 utilizes toluene as a sole carbon and energy source. Other strains of *Pseudomonas* have been previously isolated and described which metabolize or degrade toluene, including *Pseudomonas putida* mt-2 (Pp mt-2). Williams and Murry, *J. Bacteriol.* 120: 416–423 (1974) and *Pseudomonas putida* PpF1 (PpF1) (Gibson, et al. *Biochemistry* 9:1626–1630 (1970). However, the genes, the enzymes and the pathways for toluene metabolism in these various *Pseudomonas* strains are distinct and non-overlapping.

The catabolic pathway for the degradation of toluene by Pp mt-2 has been designated TOL. The genes for the TOL pathway are encoded on isofunctional catabolic plasmids found in certain strains of *Pseudomonas*. The reference plasmid for the TOL degradative pathway is pWWO originally isolated from Pp mt-2. The genetics and biochemistry of the TOL pathway are well described. Kunz and Chapman, *J. Bacteriol.* 146:179–191 (1981); Williams and Murry, *J. Bacteriol.* 120:416–423 (1974); Williams and Worsey, *J. Bacteriol.* 125:818–828 (1976); Worsey and Williams, *J. Bacteriol.* 124:7–13 (1975); Murry, et al., *Eur. J. Biochem.* 28:301–310 (1972). A brief summary of the TOL pathway is as follows: initial attack of toluene is at the methyl group which undergoes successive oxidations to form benzoic acid, which is further oxidized by formation of a cis-carboxylic acid diol, which is oxidized to form catechol, which is then degraded by enzymes of a meta cleavage pathway to acetaldehyde and pyruvate.

A second catabolic pathway for the degradation of toluene by PpF1 has been established and designated TOD. In contrast to the TOL pathway, the genes for the TOD pathway are located on the bacterial chromosome and are not plasmid-encoded. Finette, et al., *J. Bacteriol.* 160:1003–1009 (1984); Finette, Ph. D. Dissertation, The University of Texas at Austin, Library Reference No. F494 (1984). The genetics and biochemistry of the TOD pathway has been studied by Finette, et al. (supra); Finette (supra); Gibson, et al. *Biochemistry* 9:1626–1630 (1970); Kobal, et al., *J. Am. Chem. Soc.* 95:4420–4421 (1973); Ziffer, et al., *J. Am. Chem. Soc.* 95:4048–4049 (1973); Dagley, et al., *Nature* 202:775–778 (1964); Gibson, et al., *Biochemistry* 7:2653–2662 (1968). A brief summary of the TOD pathway is as follows: the initial attack of toluene is by a dioxygenase enzyme system to form (+)-cis-1(S),2(R)-dihydroxy-3-methylcyclohexa-3,5-diene(cis-toluene dihydrodiol) which is oxidized to 3-methylcatechol which is further degraded by enzymes of a meta cleavage pathway.

A third catabolic pathway for the degradation of toluene has been recently identified in PmKR1. It has been found that PmKR1 catabolizes toluene by a novel pathway which is completely different than either of the two pathways described above. Richardson and Gibson, Abst. Ann. Meet. Am. Soc. Microbiol. K54:156 (1984). The catabolic pathway for the degradation of toluene by PmKR1 has been designated TMO, because the first step in the pathway is catalyzed by a unique enzyme complex, toluene monooxygenase. The biochemistry of the enzymes and proteins of this pathway has been recently studied in detail by Whited, Ph. D. Dissertation, The University of Texas at Austin, Library Reference No. W586 (1986).

A brief summary of the TMO pathway in PMKR1 is as follows: in the initial step toluene is oxidized to p-cresol, followed by methyl group oxidation to form p-hydroxybenzoate, followed by hydroxylation to protocatechuate and subsequent ortho ring cleavage. The steps of the TMO pathway as outlined by Whited (supra) are diagrammed in FIG. 1. In the first step of the TMO pathway, toluene is converted by toluene monooxygenase to p-cresol. PmKR1 elaborates a unique multicomponent enzyme system which catalyzes this first step monooxygenase reaction. According to Whited, (supra), at least three protein components are involved: oxygenase (at least 2 subunits of 50,000 d. and 32,000 d.), ferredoxin (23,000 d.) and NADH oxidoreductase (molecular weight unknown).

At present, despite the substantial advances in the understanding of the biochemistry of the enzymes and proteins of the TMO pathway and beginning genetic studies (Yen et al. Abstract, University of Geneva EMBO Workshop, Aug. 31–Sept. 4, 1986), the art has not been provided with information regarding the genes encoding the enzymes and proteins of the toluene monooxygenase system in PmKR1 or the usefulness of such genes and gene products in certain microbial bioconversions. The art has also not been provided with microorganism host cells containing novel recombinant plasmids containing PmKR1 toluene monooxygenase genes, in which certain of these microorganism host cells express toluene monooxygenase enzyme activity at levels that exceed the activity of wildtype PmKR1 cells.

SUMMARY OF THE INVENTION

The present invention provides novel gene segments, biologically functional plasmids and recombinant plasmids, and microorganism host cells, all of which contain the PmKR1 toluene monooxygenase genes. The present invention further provides a microorganism host cell containing a novel recombinant plasmid containing PmKR1 toluene monooxygenase genes, in which the host cell expresses toluene monooxygenase enzyme activity at levels that exceed the activity of wildtype PmKR1 cells. In addition, the present invention provides a method for using transformed microorganism host cells containing the PmKR1 toluene monooxygenase genes utilized in microbial bioconversions. Thus, the present invention provides microorganisms genetically engineered to overproduce toluene monooxygenase enzymes and proteins and therefore provides a more efficient means of conducting bioconversions dependent on this enzyme system.

The present invention encompasses a biologically functional plasmid derived from PmKR1 containing toluene monooxygenase genes. This plasmid (designated pAUT1) can be transferred by conjugation to a microorganism host cell lacking the toluene monooxygenase gene system and thus unable to convert toluene to p-cresol. In a particularly preferred embodiment of the present invention, the microorganism host cell for the pAUT1 plasmid is *Pseudomonas putida* Y2101.

The present invention also encompasses the toluene monooxygenase genes which have been isolated and cloned as various DNA gene segments from PmKR1 into a suitable, autonomously-replicating plasmid vector, resulting in a series of recombinant plasmids each of which contains a toluene monooxygenase gene segment. Each such recombinant plasmid is biologically functional and can be used to transform a microorganism host cell, conferring on the microorganism host cell the ability to convert toluene to p-cresol.

The present invention further encompasses a series of such transformed microorganism host cells. In a particularly preferred embodiment of the present invention, the microorganism host cell is *E. coli* HB101, the recombinant plasmid is pMY402 and the inducer is isopropylthiogalactoside (IPTG). The pMY402 recombinant plasmid is the pMMB66EH plasmid into which has been inserted a 4.6 kb Xho I fragment encoding the PmKR1 toluene monooxygenase genes. In another particularly preferred embodiment of the present invention, the microorganism host cell is *E. coli* FM5, the recombinant plasmid is pKY287 and the inducer is heat (42° C.). The pKY287 recombinant plasmid is the pCFM1146 plasmid into which has been inserted a 4.6 kb Xho I fragment encoding the PmKR1 toluene monooxygenase genes. These resulting recombinant host cells express toluene monooxygenase enzyme activity at levels exceeding the activity of wildtype PmKR1 cells from which the toluene monooxygenase genes were isolated.

The present invention is directed to a method for certain microbial bioconversions using PmKR1 or the transformed microorganism host cells containing the PmKR1 toluene monooxygenase genes, in particular, the conversion of a selected phenyl compound to a selected phenolic compound. In a particularly preferred embodiment of the present invention, a method is provided for making p-hydroxyphenylacetic acid using the transformed microorganism host cells containing the PmKR1 toluene monooxygenase genes.

The present invention is also directed to a method for the microbial production of indigo from indole using PmKR1 cells or the transformed microorganism host cells containing the PmKR1 toluene monooxygenase genes. Further aspects and advantages of the present invention will become apparent to those skilled in the art upon consideration of the following detailed description.

BRIEF DESCRIPTION OF THE DRAWINGS

FIG. 3 illustrates a summary of recombinant plasmids, plasmid vectors and restriction maps of the PmKR1 DNA segments containing toluene monooxygenase genes.

DETAILED DESCRIPTION

Figure 1:
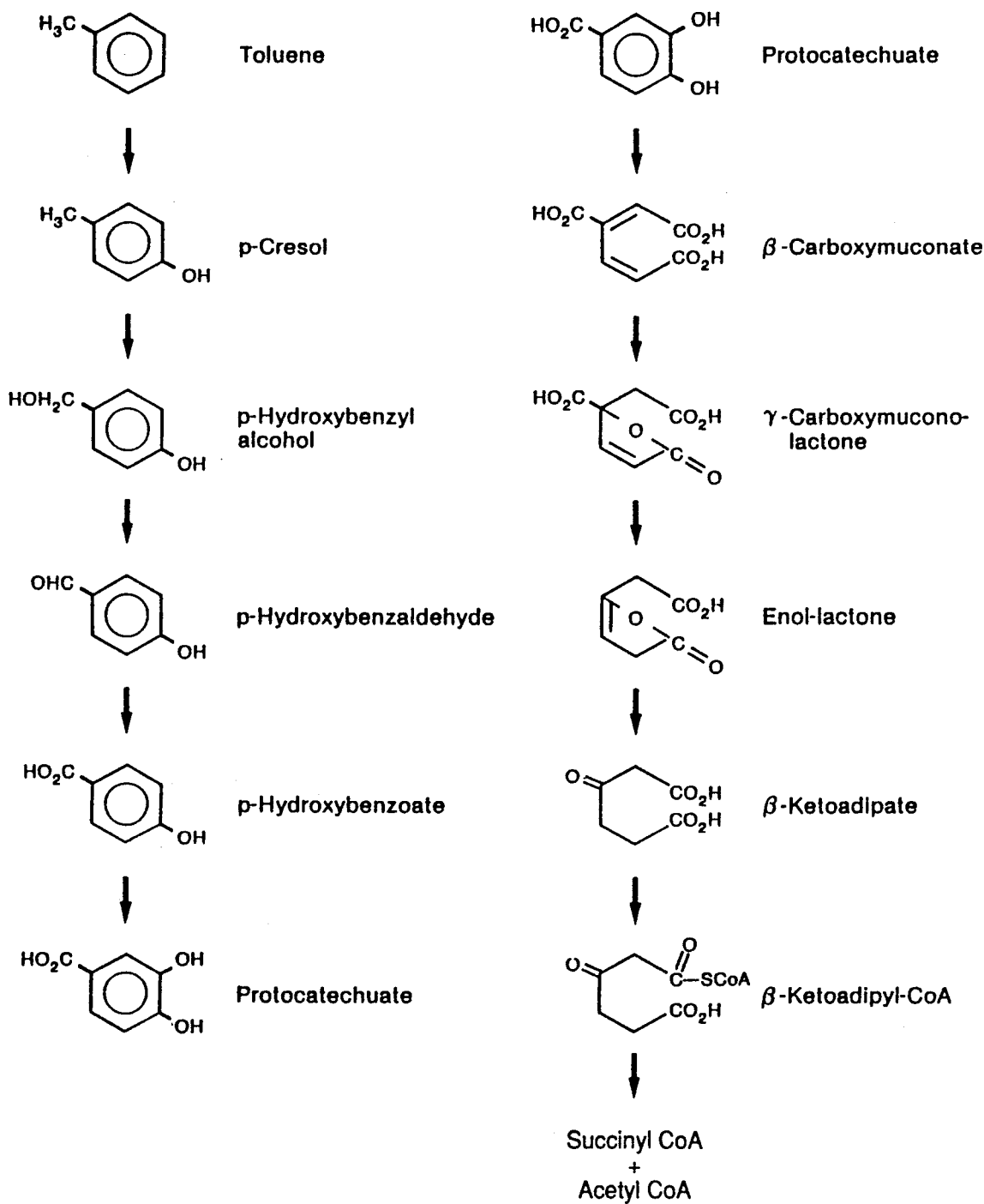
FIG. 1 illustrates the steps of the PmKR1 toluene monooxygenase (TMO) pathway.

The methods and materials that provide an illustration of the practice of the invention and that comprise the presently preferred embodiments relate specifically to plasmid-borne DNA gene segments of PmKR1 origin encoding the genes for the PmKR1 toluene monooxygenase enzyme system. By conjugation or transformation, these plasmid-borne DNA gene segments can be introduced and expressed in certain microorganism host cells. Microorganism host cells containing PmKR1 toluene monooxygenase genes are useful in a method for certain bioconversions.

The invention is now illustrated by the following Examples, with reference to the accompanying drawings. The examples do not include detailed descriptions for conventional methods employed in the isolation of DNA, the cleavage of DNA with restriction enzymes, the construction of vectors, the insertion of DNA gene segments encoding polypeptides of interest into such vectors (e.g. plasmids) or the introduction of the resulting recombinant plasmids into microorganism host cells. Such methods are well-known to those skilled in the art of genetic engineering and are described in numerous publications including the following: Maniatis et al., *Molecular Cloning-A Laboratory Manual*, Cold Spring Harbor Laboratory (1982); Davis et al., *Basic Methods in Molecular Biology*, Elsevier Science Publishing Co. (1986); *Current Protocols in Molecular Biology*, edited by Ausubel et al., Greene Publishing Associates and Wiley Interscience (1987).

EXAMPLE 1

Growth of PmKR1 Cells

*Pseudomonas mendocina* KR-1 was grown overnight at 30° in PAS medium or on a PAS agar plate (Chakrabarty, et al., *Proc. Natl. Acad. Sci. U.S.A.*, 70:1137-1140 1973) with toluene (supplied as vapor) for growth and for induction of the toluene monooxygenase genes.

EXAMPLE 2

Construction of PmKR1 Bgl II Library in *E. coli* HB101

A. Preparation of PmKR1 DNA

Total DNA was isolated from PmKR1 by conventional methods. Briefly, PmKR1 was inoculated into PAS medium containing toluene according to Example 1 and incubated with shaking at 30° C. overnight (13–17 hours). After incubation, PmKR1 cells in the stationary growth phase were collected by centrifugation. The cells were lysed and total PmKR1 DNA was then extracted and purified as described by Dhaese et al., *Nucleic Acid Res.* 7: 1837-1849 (1979).

B. Preparation of Plasmid DNA

*E. coli* HB101 containing the pRK290 plasmid (Ditta, et al., *Proc. Natl. Acad. Sci. U.S.A.* 77: 7347-7351 (1980)) was inoculated into L broth and incubated with shaking at 37° C. overnight. The bacterial cells were collected by centrifugation, lysed and the bulk of chromosomal DNA and cellular debris was removed by centrifugation. The pKR290 plasmid DNA was then purified by conventional techniques using cesium chloride/ethidium bromide density gradients.

C. Preparation of Recombinant Plasmid

Total PmKR1 DNA obtained in Part A above and pRK290 plasmid DNA obtained in Part B above were separately treated with the restriction endonuclease Bgl II, under conditions of complete digestion. The Bgl II digested PmKR1 DNA was mixed with Bgl II digested pRK290 plasmid DNA and the mixture then incubated with DNA ligase.

D. Transformation with Recombinant Plasmid

The ligated DNA obtained in Part C above was used to transform *E. coli* HB101 and the transformed cells were plated on selection plates of L-agar containing 10 μg/ml tetracycline. Only those cells which are successfully transformed and which contain the pRK290 plasmid or a recombinant pRK290 plasmid with PmKR1 DNA can grow on the selection plates. Colonies which grew on the selection plates were tested for the presence of recombinant plasmids containing PmKR1 toluene monooxygenase genes by the conjugation and complementation screening assay of Example 3.

EXAMPLE 3

Conjugation and Complementation Screening Assay

A complementation assay involving plasmid transfer via bacterial conjugation was used to screen the PmKR1 Bgl II library made according to Example 2 and the PmKR1 Sac I library made according to Example 8 in order to detect recombinant plasmids containing PmKR1 toluene monooxygenase genes. Accordingly, plasmids were transferred between bacterial strains by the conjugation ("mating") procedure described by Yen and Gunsalus, *Proc. Natl. Acad. Sci. U.S.A.*, 79:874–878 (1982) which procedure is summarized briefly as follows.

Colonies were removed from the selection plates of Example 2 or Example 8 by gentle scraping with L-broth. The resulting bacterial cell suspension was washed to remove any tetracycline and suspended in L-broth for the mating. Suspensions of donor cells, helper cells (if necessary) and recipient cells in logarithmic phase were mixed in equal volumes. Small aliquots of the mixture were placed on L-agar plates thus allowing all cell types to grow. After overnight incubation at 30° C., the cells were replated on a PAS agar selection plate containing 50 μg/ml tetracycline. Toluene was provided as sole carbon source for growth. Toluene vapor was supplied to the selection plate by taping a cotton-stoppered toluene containing tube to the lid of the plate. This selection plate permits only the desired trans-conjugates to grow. In all experiments performed, the donor cells were from an *E. coli* HB101 library (either the Bgl II library of Example 3 or the Sac I library of Example 8) carrying a recombinant plasmid (pRK290 or pKY235 containing PmKR1 gene segments) to be transferred in the mating. The helper cells used were *E. coli* HB101 cells carrying the helper plasmid pRK2013 which plasmid provided the transferring functions for those transferring plasmids which do not carry the tra genes. Alternatively, the helper plasmid pRK2013 was introduced directly into the donor cells to provide its transferring function. The recipient strain was one of several mutant strains of *Pseudomonas mendocina* KR-1 (Pm Y4001, Pm Y4002, Pm Y4007) prepared as described in Example 4. Each of the mutant strains has a defective toluene monooxygenase gene and is unable to convert toluene to p-cresol. When a recombinant plasmid containing the specific PmKR1 toluene monooxygenase gene which is defective in the recipient strain has been successfully transferred during conjugation, the resulting transconjugate will be able to grow as a colony on the selection plates containing toluene as the sole carbon source for growth.

The colonies which grew on the selection plates were purified by restreaking each colony once or twice on a selection plate. These transconjugates are further manipulated according to Example 5.

EXAMPLE 4

Preparation of *Pseudomonas mendocina* KR-1 Mutant Strains

PmKR1 cells were mutagenized and the toluene monooxygenase defective mutants were isolated according to the following protocol. Cells were grown in 5 ml of L broth to $O.D._{660}$ of approximately 0.7 and resuspended into 2 ml of 50 mM citrate buffer pH 6.0 containing N-methyl-N'-nitro-N-nitrosoguanidine (nitrosoguanidine) at a concentration of 0.2 mg per ml. After incubation at room temperature for 20 minutes, the cells were washed twice with 2 ml of 1M phosphate buffer pH 7.0 and resuspended into 50 ml of L broth. After growth overnight, the cells were streaked on L agar plates for single colonies. The individual colonies were picked and streaked onto PAS plates containing toluene or p-cresol as sole carbon source. The toluene monooxygenase defective mutants, PmY4001, PmY4002 and PmY4007 were isolated as strains which grew on p-cresol but not on toluene. The toluene monooxygenase assay as described in Example 11 further confirmed that these mutants have a defective toluene monooxygenase enzyme system.

Similar mutagenesis techniques may be used to obtain mutants defective in the enzyme p-hydroxybenzaldehyde dehydrogenase of the TMO pathway. After nitrosoguanidine treatment of PmKR1 cells as described above, p-hydroxybenzaldehyde dehydrogenase defective mutants are isolated as strains which grow on p-hydroxybenzoate but do not grow on toluene, p-cresol, p-hydroxybenzylalcohol or p-hydroxybenzaldehyde.

EXAMPLE 5

Isolation of 9.4 kb Bgl II Fragment

A number (12) of the transconjugate colonies of PmY4001 containing PmKR1 toluene monooxygenase genes isolated according to Example 3 were further characterized as follows. Each colony was grown and plasmid DNA was isolated by conventional methods. The plasmid DNA from each isolate was used to transform *E. coli* HB101 cells. The plasmid in each transformant was transferred to PmY4001 by conjugation according to Example 3 except that the selection plates contained tetracycline and glucose (2 mg/ml). Each transconjugate was tested for growth on toluene by plating the cells on PAS agar supplemented with 50 μg/ml tetracycline and toluene vapor. After the toluene monooxygenase complementing activity of the plasmid was confirmed in the transconjugates each such HB101 transformant was grown and plasmid DNA was isolated by conventional methods.

The DNA was digested with Bgl II and a 9.4 kb fragment was isolated from each transconjugate colony which complemented each PmKR1 mutant strain of Example 4 for toluene utilization. This result indicated that the 9.4 kb Bgl II fragment from PmKR1 contained one or more toluene monooxygenase genes. Two Sac I sites were mapped close to one end of the 9.4 kb Bgl II fragment.

EXAMPLE 6

Construction of pKY235 Plasmid Vector

Figure 2:
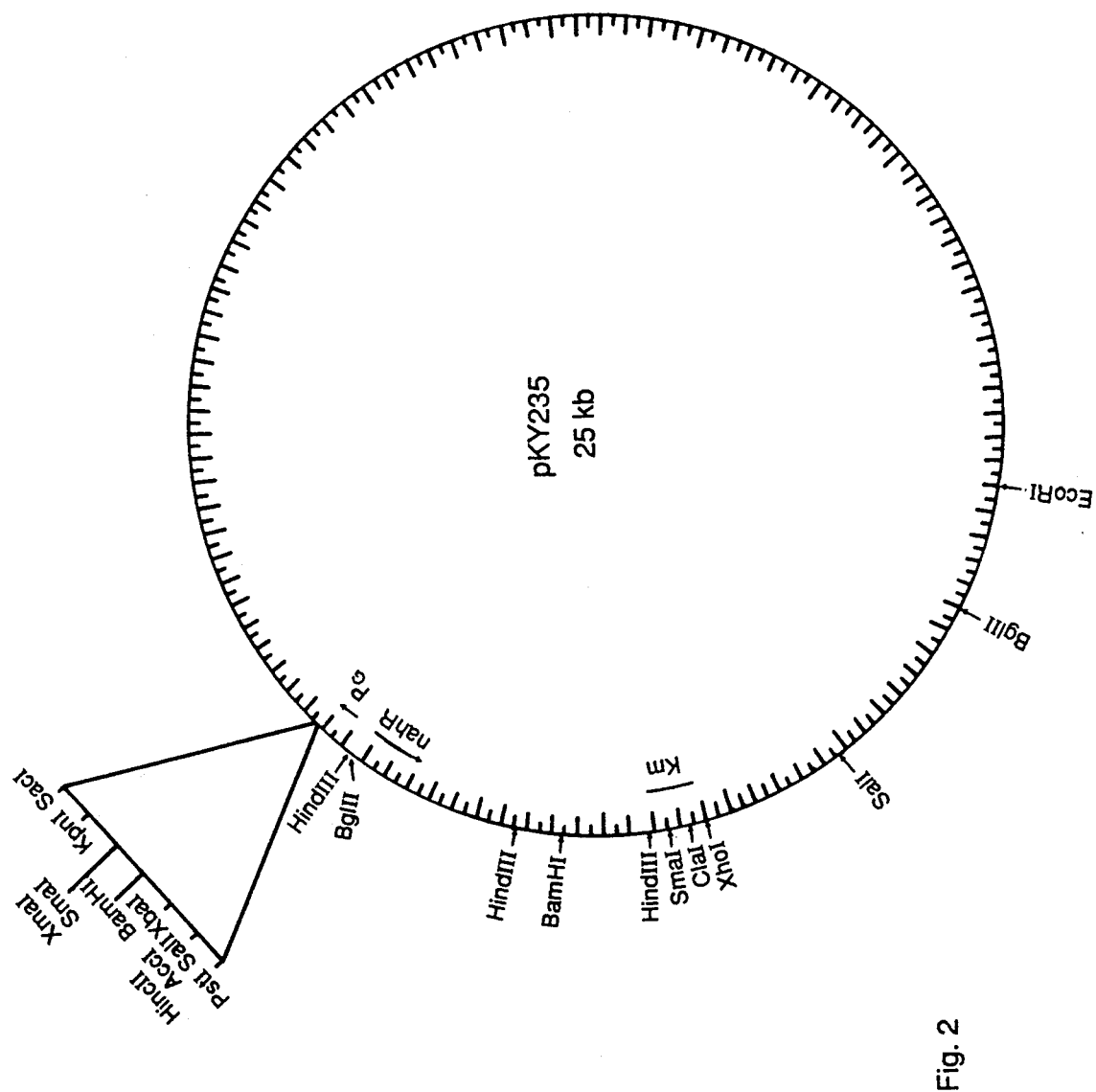
FIG. 2 shows a map of the pKY235 plasmid vector.

The starting material for the construction of the pKY235 plasmid was the pKY217 plasmid described by Yen and Gunsalus, *J. Bacteriol.* 162: 1008– 13 (1985). The pKY235 plasmid was constructed according to the following series of steps. In the first step, a 5.1 kb Hind III fragment from pKY217 containing the nahR and nahG genes was cloned into the Hind III site of the pKT240 plasmid described by Bagdasarian et al., *Gene* 26: 273-82 (1983). The resulting plasmid from this first step was designated pKY219. In the second step, an approximately 7 kb Bam HI - Sac I fragment from pKY219 containing the nahR and nahG genes was cloned into the Bam HI and Sac I sites of the pKT231 plasmid described by Bagdasarian et al. *Gene* 16: 237-47 (1981). The resulting plasmid was designated pKY223. In the next step, a 6 kb Pst I fragment from pKY223 containing the nahR gene, 200 base pairs of the nahG gene and the gene conferring kanamycin resistance was cloned into the Pst I site of the pUC19 plasmid described by Yanisch-Perron et al., *Gene* 33: 103–119 (1985). The resulting plasmid was designated pKY256. The orientation of the 6 kb Pst I fragment in pKY256 placed the multicloning site of pUC19 from the Sal I to the Eco RI site immediately downstream to the Pst I site in the nahG gene. In the final step, a 5.4 kb BstE II - Eco RI fragment from pKY256 containing the gene conferring kanamycin resistance, the nahR gene, 200 base pairs of the nahG gene and a multiple cloning site was end-filled with the large fragment of *E. coli* DNA polymerase I and inserted into the pRK290 plasmid described by Ditta et al., *Proc. Nat'l Acad. Sci. U.S.A.* 77; 7347-7351 (1980) to replace the approximately 1 kb Sma I fragment of pRK290. The resulting plasmid was designated pKY235 and a map of pKY235 is shown in FIG. 2.

EXAMPLE 7

Construction of pCFM1146 Plasmid Vector

The starting material for the construction of the pCFM1146 plasmid was the pCFM836 plasmid. A detailed description of the construction of expression vectors, including pCFM836, is described in U.S. Pat. No. 4,710,473, which is hereby incorporated by reference in its entirety. The pCFM836 plasmid contains a heat inducible promoter, a restriction site bank (cloning cluster), plasmid origin of replication, a transcription terminator, genes regulating plasmid copy number, and a gene conferring kanamycin resistance but no synthetic ribosome binding site immediately preceding the cloning cluster. The pCFM1146 plasmid ATCC number 67671 was derived from pCFM836 by substituting the small DNA sequence between the unique Cla I and Xba I restriction sites with the following oligonucleotide

| 5' | CGATTTGATT | 3' |
|---|---|---|
| 3' | TAAACTAAGATC | 5' | and by destroying the two endogenous Nde I restriction sites by cleavage with Nde I and then filling with T4 polymerase enzyme, followed by blunt end ligation.

EXAMPLE 8

Construction of PmKR1 Sac I Library in *E. coli* HB101

The pKY235 plasmid vector prepared according to Example 6 was used to construct a Sac I library in *E. coli* HB101 according to conventional techniques for constructing genomic libraries. Total DNA from PmKR1 was isolated as described in Example 2, Part A. The isolated PmKR1 DNA was treated with the restriction endonuclease Sac I under conditions of partial digestion. In order to produce a population of DNA fragments enriched in those fragments containing some or all of the PmKR1 toluene monooxygenase genes for use in constructing this Sac I library, the partially digested PmKR1 DNA was fractionated by size using a 10%–40% sucrose density gradient according to conventional procedures. After centrifugation for 24 hours at 26,000 rpm in an SW-28 centrifuge tube and rotor, the DNA fractions were collected and tested by hybridization. The 9.4 kb Bgl II fragment isolated from the Bgl II library constructed according to Example 3, known to complement each PmKR1 mutant strain for toluene utilization according to Example 5 and thus likely to contain at least one of the PmKR1 toluene monooxygenase genes, was radiolabeled and used as a probe to select hybridizing fractions from the sucrose gradient. The hybridizing fractions were pooled to provide a population of DNA fragments enriched in PmKR1 toluene monooxygenase containing fragments. This enriched population of DNA fragments was used to construct the Sac I library.

The enriched Sac I digested PmKR1 DNA was mixed with Sac I digested pKY235 plasmid DNA and incubated with DNA ligase. The ligated DNA was used to transform *E. coli* HB101 and the transformed cells were plated onto selection plates of L-agar containing 10 μg/ml tetracycline. Only those cells which were successfully transformed and containing the pKY235 plasmid or a recombinant pKY235 plasmid with PmKR1 DNA can grow on the selection plates. Transformed colonies were tested for PmKR1 toluene monooxygenase genes by the conjugation and complementation assay of Example 3.

EXAMPLE 9

Isolation of 20.5 kb Sac I Fragment

A number (10) of the transconjugates which utilized toluene as a sole carbon source were further characterized by isolating the plasmid DNA, transforming *E. coli* HB101, and conjugating into PmKY4001 to test for growth on toluene according to Example 5. An *E. coli* HB101 transformant containing a recombinant pKY235 plasmid (designated pKY266) ATCC number 67672 carrying toluene monooxygenase genes was grown and plasmid DNA was isolated by conventional methods. Restriction enzyme analysis of the insert in pKY266 plasmid indicated that it carried two Sac I fragments of 10.2 kb and 10.3 kb, respectively. The 10.2 kb Sac I fragment contains 8 kb of the 9.4 kb Bgl II fragment described in Example 5.

EXAMPLE 10

Construction of Recombinant Plasmids to Map the Toluene Monooxygenase Genes

The 10.2 kb Sac I fragment of pKY266 was further subcloned into the high-copy-number E. coli expression vector pUC19 described by Yanisch-Perron et al., Gene 33: 103–119 (1985) and the resulting recombinant plasmid was designated pKY277. The pKY277 plasmid was used to transform E. coli JM109 cells. This new E. coli strain designated JM109/pKY277, synthesized a blue pigment with properties expected of indigo in L broth. Toluene monooxygenase activity was also detected in this strain. Further mapping of the toluene monooxygenase genes correlated the indigo-producing property with the presence of toluene monooxygenase activity. (See Table I).

The 10.2 kb Sac I fragment of pKY277 was digested with a series of restriction enzymes and a partial restriction map was generated as shown in FIG. 3. Based on this restriction map, a series of DNA fragments were deleted from one end of the 10.2 kb Sac I fragment in pKY277 to generate plasmids pKY280, pKY281, pKY282 and pKY283 shown in FIG. 3. A 4.6 kb Xho I fragment of pKY282 was subcloned into the Sal I site of pUC19 to generate the plasmid pMY401. A 4.6 kb Bam HI - Sph I fragment of pMY401 containing the 4.6 kb Xho I fragment was inserted into the E. coli expression vector pUC18 described by Yanisch-Perron et al., Gene 33: 103–119 (1985) to generate the plasmid pMY404. The pUC18 plasmid is identical to pUC19 except the polycloning site is in an opposite orientation with respect to the lac promoter. As a result, the 4.6 Xho I fragment was inserted into the pUC18 plasmid in an opposite orientation to that in the pUC19 plasmid with respect to the lac promoter. The 4.6 kb Xho I fragment of pKY277 was also cloned into the broad host range plasmid vector pMMB66EH described by Furste et al., Gene 48: 119–131 (1986) to construct the plasmid pMY402. In addition, as shown in FIG. 3, a 2.2 kb Sac I - Bgl II fragment was deleted from the left end of the 5.9 kb Sac I - Xma I fragment of pKY282 by digesting pKY282 DNA with Sac I and Bgl II, filling the ends with the large fragment of E. coli DNA polymerase I and ligating the ends. The resulting plasmid was designated pMY400.

As shown in Table I (according to the assay of Example 11), pMY402 containing cells responded to IPTG for induction of the toluene monooxygenase genes. This result located the toluene monooxygenase genes in the 4.6 kb Xho I fragment and revealed the direction of transcription of the toluene monooxygenase genes as from left to right shown in FIG. 3. The difference in the orientation of the 4.6 kb Xho I fragment in pMY401 and pMY404 as well as the difference in toluene monooxygenase activity in pMY401 and pMY404 containing cells (Table I) are also consistent with this transcriptional direction of the toluene monooxygenase genes. In order to express the toluene monooxygenase genes at a high level, the 4.6 kb Xho I fragment of pKY282 was also cloned into the Xho I site of the E. coli expression vector pCFM1146 (as described in Example 7) to construct pKY287.

EXAMPLE 11

Toluene Monooxygenase Assay

Cells were grown in PAS medium containing 0.4% glutamate or in L broth to saturation. They were resuspended into an appropriate volume of the same medium to an $O.D._{660}$ of 3.0. An aliquot of the cells was used for the determination of protein concentration by the method of Bradford, Anal. Biochem. 72: 248 (1976) using the Bio-Rad Protein Assay. An aliquot of 0.5 ml of cells was mixed with 4 μmoles of p-cresol in 10 μl and 15 nmole of radioactive toluene (toluene-ring-$^{14}$C, Sigma Chemical Co., 56.3 mCi/mmole) in 5 μl and the mixture was incubated at room temperature with occasional vortexing for 20 minutes. After incubation, 20 μl of the mixture were spotted on a small piece of a thin-layer chromatography plate and the plate was air-dried for twenty was determined in a liquid scintillation counter and was used to calculate the amount of toluene degradation product on the plate and the specific activity of toluene monooxygenase. The results are presented in Table I.

TABLE I

Expression of the Toluene Monooxygenase (TMO) genes in E. coli and P. mendocina

| Plasmid | Inducer | Host Cell | Specific Activity of TMO (nmole min$^{-1}$ mg$^{-1}$) | Indigo Formation |
|---|---|---|---|---|
| pAUT1 | Toluene | P. mendocina KR1 | 0.130 | + |
| pAUT1 | None | P. mendocina KR1 | 0.010 | + |
| pKY266 | None | P. putida KT2440 | 0.020 | + |
| pKY277 | None | E. coli JM109 | 0.010 | + |
| pMY405 | None | E. coli HB101 | 0.005 | − |
| pMY405 | IPTG | E. coli HB101 | 0.015 | + |
| pKY280 | None | E. coli JM109 | 0.010 | + |
| pKY281 | None | E. coli JM109 | 0.010 | + |
| pKY282 | None | E. coli JM109 | 0.010 | + |
| pKY283 | None | E. coli JM109 | 0.005 | − |
| pMY400 | None | E. coli JM83 | 0.005 | − |
| pMY401 | None | E. coli JM83 | 0.035 | + |
| pMY404 | None | E. coli JM83 | 0.010 | + |
| pMY402 | None | E. coli HB101 | 0.005 | − |
| pMY402 | IPTG | E. coli HB101 | 0.200 | + |
| pMY287 | Heat | E. coli FM5 | 0.500 | + |
| pUC19 | None | E. coli JM109 | 0.005 | − |
| pMMB66EH | IPTG | E. coli HB101 | 0.005 | − |
| pFCM1146 | Heat | E. coli FM5 | 0.005 | − |

EXAMPLE 12

Conversion of Certain Phenyl Compounds to Certain Phenolic Compounds

A. Conversion by PmKR1 Cells

Many phenyl compounds, including toluene, methylphenylacetic acid, ethylphenylacetic acid, 2-phenylethanol, acetanilide, fluorobenzene and ethylbenzene, may serve as substrates and thus be converted to phenolic compounds via para-hydroxylation by the toluene monooxygenase system of PmKR1. The following schemes illustrate several possible conversions:

SCHEME A $$\underset{\text{I}}{\text{CH}_3\text{-C}_6\text{H}_5} \longrightarrow \underset{\text{II}}{\text{CH}_3\text{-C}_6\text{H}_4\text{-OH}}$$

wherein:

I is toluene
II is p-cresol

SCHEME B $$\underset{\text{III}}{\text{CH}_2\text{COOCH}_3\text{-C}_6\text{H}_5} \longrightarrow \underset{\text{IV}}{\text{CH}_2\text{COOCH}_3\text{-C}_6\text{H}_4\text{-OH}}$$

wherein:

III is methylphenylacetic acid
IV is p-hydroxymethylphenylacetic acid

SCHEME C $$\underset{\text{V}}{\text{CH}_2\text{CH}_2\text{OH-C}_6\text{H}_5} \longrightarrow \underset{\text{VI}}{\text{CH}_2\text{CH}_2\text{OH-C}_6\text{H}_4\text{-OH}}$$

wherein:

V is 2-phenylethanol
VI is p-hydroxy-2-phenylethanol

For each conversion, a phenyl compound substrate (for example, Formulas I, III or V) was mixed with PmKR1 cells, incubated for a period sufficient to effect the bioconversion and then assayed for the presence of phenolic compounds as follows.

*Pseudomonas mendocina* KR1 cells were grown at 25° C.-30° C. in 50 ml PAS medium supplemented with 0.4% glutamate to stationary phase (12–16 hours) n the presence (induced) or absence (uninduced) of toluene vapor supplied from 2.5 ml toluene. An aliquot of 5–50 ml cells were resuspended into the same volume of the same medium or concentrated 2.5 fold in the same medium. A given amount of the substrate equivalent to form a 15–30 mM solution was mixed with the cells and the mixture was incubated at 25° C.-30° C. with vigorous shaking for 1–24 hours. Typically the mixture was incubated for 5-6 hours Formation of phenolic compounds was determined according to the assay method of Gupta et al., *Clin. Biochem.* 16 (4): 220–221 (1983). The assay results for conversion of several phenyl substrates to phenolic compounds at various times and temperatures of incubation are shown in Table II.

TABLE II

| Synthesis of Phenolic Compounds by Toluene Monooxygenase of *Pseudomonas mendocina* KR1 | |
|---|---|
| Substrate (Time and Temperature of Incubation) | $O.D._{660}$ reading in Assay |
| acetanilide (6 hrs., 25° C.) | 1.07 |
| fluorobenzene (24 hrs., 25° C.) | 0.73 |
| methylphenylacetate (6 hrs., 30° C.) | 0.23 |
| ethylphenylacetate (6 hrs., 30° C.) | 0.13 |
| ethylbenzene (6 hrs., 30° C.) | 0.37 |
| 2-phenylethanol (5 hrs., 30° C.) | 0.16 |
| substrate in uninduced culture | 0.03 |

B. Conversion by Microorganism Host Cells Containing Recombinant Plasmids encoding PmKR1 Toluene Monooxygenase Genes The same conversions according to Part A may be accomplished by using microorganism host cells containing the recombinant plasmids of Example 10. Any of the recombinant plasmids (except pKY283 or pMY400) which encode functional PmKR1 toluene monooxygenase genes may be used to transform an appropriate microorganism host cell as described in Example 10. A preferred method is to use pMY402 as the recombinant plasmid, *E. coli* HB101 as the microorganism host cell and IPTG as the inducer, as described in Example 11. The resulting strain was designated HB101/pMY402. Another preferred method is to use pKY287 as the recombinant plasmid, *E. coli* FM5 ATCC number 53911 as the microorganism host cell and heat (42° C. for 1–3 hrs). as the inducer. The resulting strain was designated FM5/pKY287.

For each conversion, a phenyl compound (for example, Formulas I, III or V) is mixed with HB101/pMY402 or FM5/pKY287 cells. The mixture is incubated for a period sufficient to effect the bioconversion and then assayed as described in Part A for the presence of phenolic compounds. For each bioconversion with HB101/pMY402 cells, the cells must be grown and assayed in the presence of IPTG to induce PmKR1 toluene monooxygenase activity as follows. Cells are grown in PAS medium containing 0.4% glutamate and 1 mM IPTG or grown in L broth with 1 mM IPTG to saturation. The cells are resuspended in an appropriate volume of the same medium to an $O.D._{660}$ of 3.0 and incubated with substrate and assayed as described in Part A. For each bioconversion with FM5/pKY287 cells, the cells must be grown under the following temperature conditions to induce PmKR1 toluene monooxygenase activity. FM5/pKY287 cells are grown in L broth to an $OD_{660}$ of 0.4. The cultures are incubated with shaking at 42° C. for 3 hours and then shifted to 30° C. to incubate for another 2 hours. Cells are resuspended in fresh L broth to an $O.D._{660}$ of 3.0 and incubated with substrate and assayed as described in Part A.

EXAMPLE 13

Conversion of Toluene to p-Hydroxyphenylacetic Acid

A. Conversion by PmKR1 Cells

For the conversion of toluene substrate to p-hydroxyphenylacetic acid, toluene is mixed with a PmKR1 mutant containing defective p-hydroxybenzaldehyde dehydrogenase as described in Example 4 and incubated for a period sufficient to effect the conversion of toluene to p-hydroxybenzyl alcohol. In the second step, the cell mixture containing the p-hydroxybenzyl alcohol intermediate is reacted with nickel (Ni) and carbon monoxide (CO) in such concentrations and at such temperatures sufficient to convert the p-hydroxybenzyl alcohol to p-hydroxyphenylacetic acid, according to the methods of U.S. Pat. Nos. 4,482,497; 4,659,518; 4,631,348, which are hereby incorporated by reference. The conversion scheme is illustrated as follows:

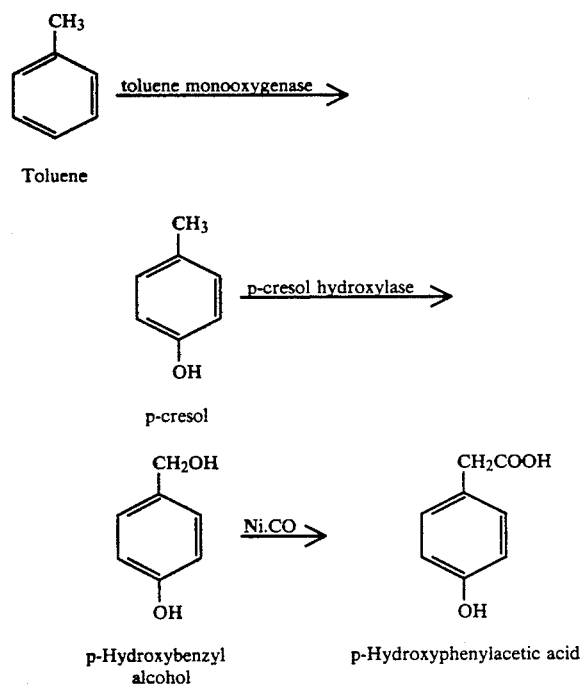

B. Conversion by Microorganism Host Cells Containing Recombinant Plasmids encoding PmKR1 Toluene Monooxygenase Genes The same conversion according to Part A may be accomplished by using microorganism host cells containing the p-cresol hydroxylase gene and the recombinant plasmids of Example 10. The p-cresol hydroxylase gene may be cloned by conventional genetic engineering techniques from a variety of microorganisms containing this gene, including for example, from PmKR1 or from plasmid pND50 (Hewetson et al., *Genet. Res. Camb.* 32: 249–255, 1978). Any of the recombinant plasmids (except pKY283 or pMY400) which encode functional PmKR1 toluene monooxygenase genes may be used to transform an appropriate microorganism host cell described in Example 10. A preferred method is to use HB101/pMY402 cells. Another preferred method is to use FM5/pKY287 cells.

For the conversion as illustrated in Part A, toluene is mixed with HB101/pMY402 cells grown and induced with IPTG or FM5/pKY287 cells grown and induced with heat as described in Example 12. The mixture is incubated for a period sufficient to effect the conversion of toluene to p-hydroxybenzyl alcohol, and then is reacted with Ni and CO according to Part A to effect the conversion to p-hydroxyphenylacetic acid.

EXAMPLE 14

Conversion of Methylphenylacetic Acid to p-Hydroxyphenylacetic Acid

A. Conversion by PmKR1 Cells

For the conversion of methylphenylacetic acid substrate to p-hydroxyphenylacetic acid, methylphenylacetic acid is mixed with PmKR1 grown as described in Example 12 and incubated for a period sufficient to effect the conversion of methylphenylacetic acid to p-hydroxymethylphenylacetic acid. In the second step, the cell mixture containing the p-hydroxyphenylacetic acid intermediate is subjected to acid hydrolysis at acid concentrations and temperatures sufficient to convert the p-hydroxymethylphenylacetic acid to p-hydroxyphenylacetic acid. The conversion scheme is illustrated as follows:

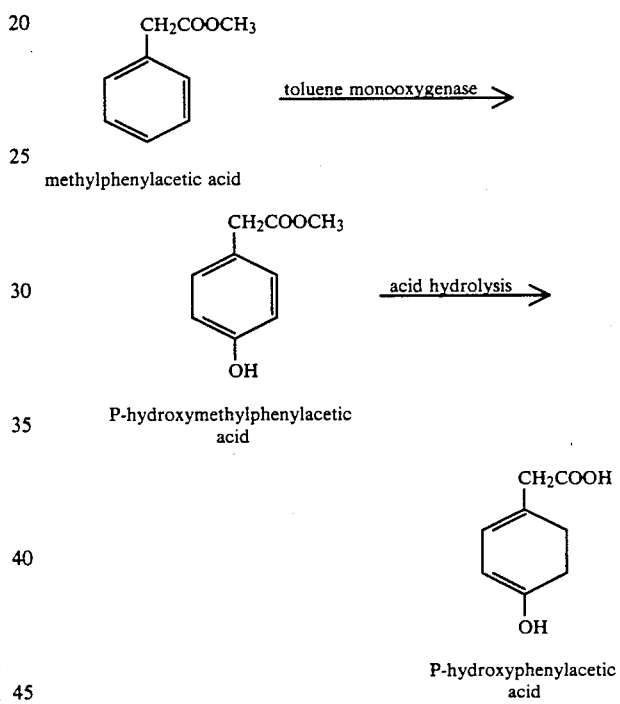

B. Conversion by Microorganism Host Cells Containing Recombinant Plasmids encoding PmKR1 Toluene Monooxygenase Genes The same conversion according to Part A may be accomplished by using microorganism host cells containing the recombinant plasmids of Example 10. Any of the recombinant plasmids (except pKY283 or pMY400) which encode functional PmKR1 toluene monooxygenase genes may be used to transform an appropriate microorganism host cell described in Example 10. A preferred method is to use HB101/pMY402 cells. Another preferred method is to use FM5/pKY287 cells.

For the conversion as illustrated in Part A, methylphenylacetic acid is mixed with HB101/pMY402 cells grown and induced with IPTG or FM5/pKY287 cells grown and induced with heat as described in Example 12. The mixture is incubated for a period sufficient to effect the bioconversion of p-hydroxymethylacetic acid and then the mixture is subjected to acid hydrolysis at acid concentrations and temperatures sufficient to yield p-hydroxyphenylacetic acid.

EXAMPLE 15

Conversion of Indole to Indigo

A. Conversion by PmKR1 Cells

For the conversion of indole substrate to indigo, 50 μg/ml indole was mixed with PmKR1 cells grown as described in Example 12 and incubated for a period sufficient to effect the conversion of indole to indigo, generally 48 hours. The indigo may be isolated from the cell mixture by the procedure described by Ensley in Example 5 of U.S. Pat. No. 4,520,103.

B. Conversion by Microorganism Host Cells Containing Recombinant Plasmids encoding PmKR1 Toluene Monooxygenase Genes The same conversion according to Part A may be accomplished by using microorganism host cells containing the recombinant plasmids of Example 10. Any of the recombinant plasmids (except pKY283 or pMY400) which encode functional PmKR1 toluene monooxygenase genes may be used to transform an appropriate microorganism host cell described in Example 10. A preferred method is to use HB101/pMY402 cells. Another preferred method is to use FM5/pKY287 cells.

For the conversion as illustrated in Part A, indole is mixed with HB101/pMY402 cells grown and induced with IPTG or FM5/pKY287 cells grown and induced with heat as described in Example 12. The mixture is incubated for a period sufficient to effect the bioconversion of indole to indigo. The indigo may be isolated from the cell mixture according to the procedure of Part A.

What is claimed is:

1. A plasmid derived from *Pseudomonas mendocina* KR-1 comprising the toluene monooxygenase genes, said plasmid being capable of transferring the ability to convert toluene to p-cresol to a microorganism host cell.

2. A microorganism host cell of the genus *Pseudomonas* which comprises the plasmid according to claim 1.

3. A microorganism host cell according to claim 2 wherein the *Pseudomonas* is *Pseudomonas putida* Y2101.

4. A recombinant plasmid comprising a DNA segment encoding toluene monooxygenase genes isolated from *Pseudomonas mendocina* KR-1.

5. A recombinant plasmid according to claim 4 wherein the recombinant plasmid is capable of conferring the ability to convert toluene to p-cresol to a microorganism host cell.

6. A recombinant plasmid according to claim 4 wherein the plasmid is selected from the group consisting of pUC18, pUC19, pKY235, pMMB66EH, pMMB66HE and pCFM1146.

7. A recombinant plasmid according to claim 4 wherein the DNA segment is a 20.5 kb SacI fragment having the restriction map set forth in FIG. 3 or a subfragment thereof which upon expression results in a functional toluene monooxygenase.

8. A recombinant plasmid according to claim 4 wherein the DNA segment is a 10.2 kb Sac I fragment having the restriction map set forth in FIG. 3.

9. A recombinant plasmid according to claim 4 wherein the DNA segment is a 7.7 kb Sac I-Bam I fragment having the restriction map set forth in FIG. 3.

10. A recombinant plasmid according to claim 4 wherein the DNA segment is a 6.2 kb Sac I-Sph I fragment having the restriction map set forth in FIG. 3.

11. A recombinant plasmid according to claim 4 wherein the DNA segment is a 5.9 kb Sac I-Xma I fragment having the restriction map set forth in FIG. 3.

12. A recombinant plasmid according to claim 4 wherein the DNA segment is a 4.6 kb Xho I fragment having the restriction map set forth in FIG. 3.

13. A microorganism host cell transformed with the recombinant plasmid according to claim 4.

14. A microorganism host cell according to claim 13 wherein said microorganism host cell is selected from the group consisting of *E. Coli* JM109, JM83, HB101, and FM5.

15. A microorganism host cell transformed with the recombinant plasmid according to claim 7.

16. A microorganism host cell transformed with the recombinant plasmid according to claim 8.

17. A microorganism host cell transformed with the recombinant plasmid according to claim 9.

18. A microorganism host cell transformed with the recombinant plasmid according to claim 10.

19. A microorganism host cell transformed with the recombinant plasmid according to claim 11.

20. A microorganism host cell transformed with the recombinant plasmid according to claim 12.

21. A DNA sequence comprising the 20.5 kb SacI fragment encoding the toluene monooxygenase genes isolated from *Pseudomonas mendocina* KR-1 having the restriction map set forth in FIG. 3, or a subfragment thereof, which upon expression results in a functional toluene monooxygenase.

* * * * *